United States Patent
Mertelmeier

(10) Patent No.: US 7,463,713 B2
(45) Date of Patent: Dec. 9, 2008

(54) MAMMOGRAPHY METHOD AND APPARATUS FOR GENERATING DIGITAL TOMOSYNTHETIC 3D IMAGE

(75) Inventor: Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 196 days.

(21) Appl. No.: 11/437,887

(22) Filed: May 18, 2006

(65) Prior Publication Data

US 2006/0269041 A1    Nov. 30, 2006

(30) Foreign Application Priority Data

May 18, 2005   (DE)   ................. 10 2005 022 899

(51) Int. Cl.
*A61B 6/02* (2006.01)
(52) U.S. Cl. ........................... 378/22; 378/37
(58) Field of Classification Search ............. 378/21–27, 378/37, 62, 98.8, 98.12, 108–112
See application file for complete search history.

(56) References Cited

U.S. PATENT DOCUMENTS

| | | | |
|---|---|---|---|
| 6,002,739 A * | 12/1999 | Heumann | 378/8 |
| 6,459,765 B1 | 10/2002 | Ganin et al. | |
| 6,487,271 B1 * | 11/2002 | Laurent | 378/98.9 |
| 6,529,575 B1 * | 3/2003 | Hsieh | 378/4 |
| 6,795,526 B2 | 9/2004 | Kump et al. | |
| 2004/0013229 A1 * | 1/2004 | Alving et al. | 378/49 |
| 2005/0002550 A1 * | 1/2005 | Jabri et al. | 382/131 |
| 2005/0226375 A1 * | 10/2005 | Eberhard et al. | 378/62 |

OTHER PUBLICATIONS

Wu et al., Tomographic mammography using a limited number of low-dose cone-beam projection images, Mar. 2003, Medical Physics, vol. 30, No. 3, pp. 365-380.*
Niklason et al., Digital Tomosynthesis in Breast Imaging, 1997, Radiology, vol. 205, pp. 399-406.*
Pye et al., Is there an angle to using Automated X-ray Inspection?, Dec. 2004, Technical Paper, http://www.teradyne.com/atd/resource/product/xstation.html, pp. 1-8.*
Claus et al., A new method for 3D reconstruction in digital tomosynthesis, 2002, Medical Imaging 2002: Image Processing, Proceedings of the SPIE vol. 4684, pp. 814-824.*
Wu et al., A comparison of reconstruction algorithms for breast tomosynthesis, Sep. 2004, Medical Physics, vol. 31, No. 9, pp. 2636-2647.*
"Tomographic Mammography Using a Limited Number of Low-Dose Cone-Beam Projection Images," Wu et al, Med. Phys. vol. 30 (Mar. 2003) pp. 365-380.

* cited by examiner

*Primary Examiner*—Chih-Cheng Kao
*Assistant Examiner*—John M Corbett
(74) *Attorney, Agent, or Firm*—Schiff Hardin LLP

(57) ABSTRACT

In a method and a device for generating a digital tomosynthetic 3D X-ray image of an examined object, a number of individual images are made of the examined object at different projection angles relative to the normal of the patient examination table by moving the X-ray tube. In a starting position, the X-ray tube is operated with a dose that is lower than that used for subsequent individual images. At least one preliminary image is recorded at the starting position, which is then evaluated to determine the radiographic parameters required for the recording of the subsequent individual images.

9 Claims, 2 Drawing Sheets

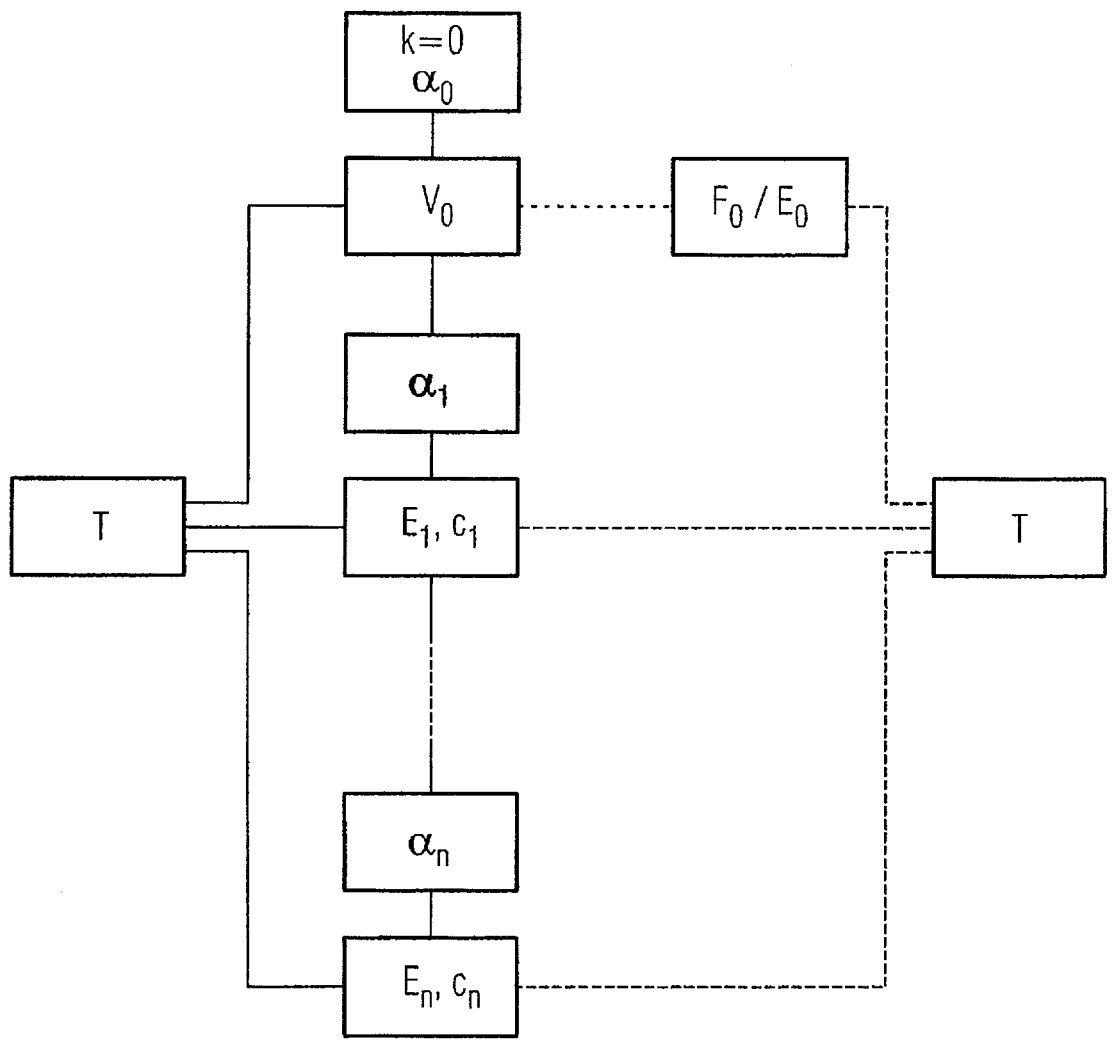

MAMMOGRAPHY METHOD AND APPARATUS FOR GENERATING DIGITAL TOMOSYNTHETIC 3D IMAGE

BACKGROUND OF THE INVENTION

1. Field of the Invention

The present invention relates to a method and a device used to generate a digital tomosynthetic 3D X-ray image of an examined object, particular in mammography.

2. Description of the Prior Art

When an X-ray image of an examined object is being prepared, for example, for mammography, it must ensure that the radiographic parameters, particularly the exposure time, are set correctly so as to guarantee an image quality suitable for diagnostic evaluation. In order to limit the exposure of the area of the examined object that is being irradiated to the minimum radiation required for diagnostic purposes, it is desirable to be able to correctly set the radiographic parameters with only one attempt. For this purpose, a so-called automatic exposure control (AEC) is conventionally used. In analog mammography, as seen in the direction of propagation of the X-rays, a number of solid-state detectors are arranged behind the X-ray film. These detectors measure the intensity of the X-rays transmitted through the X-ray film and their output signals are then used to control the radiographic parameters (for example, exposure time, operation voltage of the X-ray tube, tube current, and the anode filter combination).

With continually improving imaging techniques, a goal is to generate X-ray images with a high diagnostic relevance using the smallest X-ray doses possible. For example, the imaging techniques must still be able to distinguish benign changes from malignant changes in mammography and should reduce the number of false findings, i.e., the number of suspect findings that are not caused by malignant changes, and the number of undiscovered malignant tumors. In the case of the conventional analog X-ray mammography, a two-dimensional single image of the compressed breast in a single projection direction is generated. In such a projection the subsequent tissue layers in the direction of the X-ray are superimposed, and thus strongly absorbing benign structures may cover a malignant tumor and make the identification thereof more difficult.

In order to avoid this situation and others like it, T. Wu et al., Tomographic mammography using a limited number of low-dose cone-beam projection images; Med. Phys. 30, 365 (2003) discloses a mammography method called tomosynthesis, by means of which individual images of the female breast are obtained at different projection directions using a digital X-ray detector. Using these individual digital images that have been obtained at different projection directions, or rather the image data pertaining to these individual images, a number of slice images are reconstructed that reproduce the layers of the breast that are oriented parallel to the reception surface of the X-ray detector. In the following, such image records obtained by reconstruction will be called tomosynthetic 3D X-ray images. These measures allow one to recognize the tissue structures to be recognized better than in a conventional single projection radiograph.

In X-ray tomosynthesis, however, it is not possible to attain a suitable degree of exposure control due to the higher absorption of the digital X-ray detectors used in tomosynthesis.

SUMMARY OF THE INVENTION

An object of the present invention is to provide a method to record a digital X-ray image of an examined object, in which the aforementioned disadvantage is eliminated. It is also an object of the present invention to provide a device and a computer program product to implement such a method.

The above object is achieved in accordance with the invention by a method for the generation of a digital tomosynthetic 3D X-ray image of an examined object, using an X-ray tube and a digital X-ray detector, wherein a number of individual images with different projection angles relative to the normal of the patient examination are obtained by moving the X-ray tube, and the images are merged to create a tomosynthetic 3D X-ray image. When the X-ray tube is in a starting position it is operated with a dose that is smaller than the dose used to make the individual images, in order to produce at least one preliminary image, which is then evaluated to determine the radiographic parameters required for the subsequent individual images. This procedure ensures a correct exposure when making a digital tomosynthetic X-ray image.

In an embodiment of the method according to the invention, the dose is used as one of the radiographic parameters and is weighted for each projection angle with a weighting factor that depends on the angle and, when the X-ray tube is moved on a circular path around the examined object, is determined by the relation $c_k = 1/\cos \alpha k$, where $\alpha_k$ indicates the angle relative to the normal. Such a weighting factor $c_k$ ensures a correct exposure even for X-rays that fall obliquely on the reception surface of the X-ray detector.

In a preferred embodiment of the method, the preliminary image is recorded with a spatial resolution that equals the spatial resolution of the subsequent individual images. This makes it possible to use the preliminary image, which has been made for the purpose of determining the radiographic parameters, in the tomosynthetic reconstruction process, while taking into account the radiographic parameters set for this preliminary image, doing so either directly or by merging the image With a subsequent image that has been made in the starting position while taking into account the radiographic parameters determined for such a starting position, in order to create a complete individual image pertaining to this starting position.

As an alternative, the preliminary image can be made with a spatial resolution that is lower than the spatial resolution with which the individual images are made. This alternative enables a quicker reading and evaluation of the preliminary image.

The above object also is achieved in accordance with the present invention by a mammography apparatus that operates according to the method described above.

The above object also is achieved in accordance with the present invention by a computer program product, in the form of a computer-readable medium encoded with computer program data, for causing a mammography apparatus to operate according to the inventive method described above.

DESCRIPTION OF THE DRAWINGS

FIG. 2 is a flowchart of an embodiment of the method according to the invention.

DESCRIPTION OF THE PREFERRED EMBODIMENTS

Figure 1:
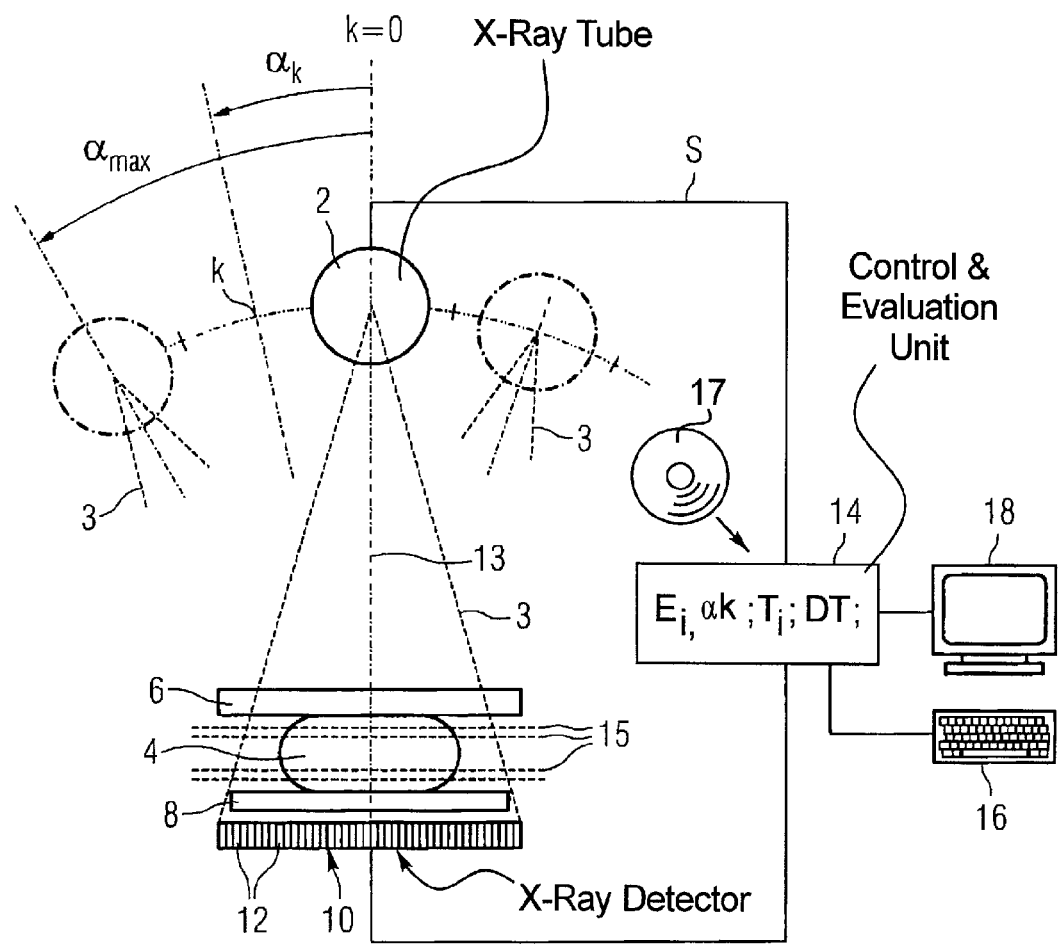
FIG. 1 shows an embodiment of a device according to the invention in a schematic illustration.

As shown in FIG. 1, a mammography device has an X-ray tube 2 for the generation of an X-ray beam 3 that passes through an examined object. The examined object 4 in this case is a female breast, which is held between a compression plate 6 and a patient examination table 8. As the X-ray tube is moved through a number of projection angles, X-ray beams pass through the examined object 4, the compression plate 6, and the patient examination table 8, are received by a large-surface digital X-ray detector 10, which is composed of a number of individual detectors 12 arranged in a matrix-like array. The X-ray tube 2 can be rotated from a starting position k=0 through various angle positions k up to a maximum projection angle of $\alpha_{max}$ (maximum displacement), so that individual images $E_k$ of the examined object 4 can be made at different projection angles $\alpha_k$ relative to the normal 13 of the patient examination table 8 of the X-ray detector 10. In the starting position k=0 (projection angle $\alpha_0$), a preliminary image $V_0$ is made with a reduced X-ray dose, which is subsequently evaluated in a control and evaluation unit 14 that contains an image processor, in order to determine the radiographic parameters required for the correct exposure of the subsequent individual images $E_k$. The subsequently obtained, correctly exposed individual images $E_k$ are combined into a tomosynthetic 3D X-ray image T by computational reconstruction in the control and evaluation unit 14. This tomosynthetic 3D X-ray image is formed by a number of slice images that reproduce various object planes 15 parallel to the patient examination table 8.

The control and evaluation unit 14 is operated with a computer-readable medium, shown in FIG. 1 as a CD-ROM 17, to implement the method described herein.

The angular position k of the X-ray tube 2 and its operation parameters are controlled by control signals S that are generated by the control and evaluation unit 14. Using input and indication elements, such as a keyboard 16 and a monitor 18, the user can select and execute numerous method variants, which will subsequently be explained. As an alternative to the exemplary embodiment illustrated in the FIG. 1 with a stationary X-ray detector 10, the X-ray tube 2 and the X-ray detector 10 can be jointly moved around a stationary examined object 4.

As shown in FIG. 2, as a first step a preliminary image $V_0$ is made with a reduced dose at a projection angle of $\alpha_0$ in a starting position k=0. Using this preliminary image $V_0$, radiographic parameters are determined for the individual images $E_0$-$E_n$ that are required for the generation of a tomosynthetic 3D X-ray image T. For this purpose, it is necessary to determine the dose required to generate a correctly exposed individual image $E_0$ in the starting position k=0. Subsequently, either an individual image $E_0$ is made in the starting position k=0, or the X-ray tube is displaced to an angular position pertaining to the projection angle $\alpha_1$, and an individual image $E_1$ is made in this position, wherein the correct dose for this position, for example, the exposure time (irradiation time) with constant other radiographic parameters (X-ray tube voltage, anode filter combination), is weighted with a weighting factor $c_1$ pertaining to this projection angle $\alpha_1$. This weighting factor is determined by the relation $c_k=1/\cos\alpha_k$, when the starting position corresponds to a projection angle $\alpha_0=0°$ and the X-ray tube is moved along a circular path. In this manner, n individual images $E_1$ to $E_n$ are made. As is illustrated in the left half of FIG. 2, these images are combined, together with the preliminary image $V_0$, to form a tomosynthetic 3D X-ray image T.

Alternatively, the projection angle $\alpha_0$ in the starting position k=0 can represent the maximum displacement $\alpha_{max}$ to one side. In this case, the pertaining individual image $E_0$ is made immediately after the preliminary image $V_0$ with the exposure time calculated from the preliminary image $E_0$. In the next steps, the X-ray tube is gradually swung to projection angles $\alpha_1$ to $\alpha_n$ and individual images $E_1$ to $E_n$ are recorded.

If in the starting position k=0 the preliminary image $V_0$ is obtained with a spatial resolution equal to that of an individual image $E_0$; then at this starting position k=0 a subsequent image $F_0$ can be made, which is combined with the preliminary image $V_0$ to form the individual image $E_0$. It is also possible to produce a high-resolution preliminary image $V_0$ that can be directly used in the tomosynthetic reconstruction.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating a digital tomosynthetic 3D X-ray image of an examination object, comprising the steps of:

moving an X-ray tube through a plurality of projection angles along a circular path relative to an examination object, and irradiating the examination object with X-rays from said X-ray tube at each of said projection angles, and detecting X-rays attenuated by the examination object with a digital X-ray detector, to generate respective images of the examination object at said projection angles, said projection angles including a first of said projection angles at a starting position of movement of said X-ray tube;

only at said first of said projection angles, irradiating the examination object with X-rays from the X-ray tube at a dose that is lower than a dose employed at others of said projection angles, to generate a preliminary image of the examination object;

automatically electronically evaluating said preliminary image to identify weighted doses for said X-ray tube for generating respective images in a remainder of said images, and automatically calculating the respective weighting factors at projection angles other than at said starting position as $c_k=1/\cos\alpha_k$, wherein $c_k$ is the weighting factor and $\alpha_k$ is the projection angle and operating said X-ray tube with said weighted doses respectively at projection angles other than said first of said projection angles to generate said remainder of said images; and computationally reconstructing a digital tomosynthetic 3D X-ray image of the examination object at least from said remainder of said images.

2. A method as claimed in claim 1 comprising generating said preliminary image with a spatial resolution equal to a spatial resolution at which said remainder of images are generated.

3. A method as claimed in claim 2 comprising using said preliminary image, together with said remainder of images, to computationally reconstruct said digital tomosynthetic 3D X-ray image.

4. A method as claimed in claim 1 comprising generating said preliminary image with a spatial resolution that is lower than a spatial resolution of said remainder of images.

5. A method as claimed in claim 4 comprising, in addition to said preliminary image, generating a subsequent image of the examination object with said X-ray tube at said starting position, and automatically electronically combining said preliminary image and said subsequent image to obtain a combined image, and using said combined image together with said remainder of images to computationally generate said digital tomosynthetic 3D X-ray image.

6. A method as claimed in claim 1 wherein said examination object is disposed on a patient examination table, and generating said preliminary image at a projection angle of 0° relative to the normal of said patient examination table.

7. A method as claimed in claim 1 wherein said X-ray tube is movable through said projection angles to a maximum projection angle representing a largest displacement of said X-ray tube, and generating said preliminary image at said maximum projection angle.

8. An apparatus for generating a digital tomosynthetic 3D X-ray image of an examination object, comprising:
- an X-ray tube movable through a plurality of projection angles along a circular path relative to an examination object, that irradiates the examination object with X-rays from said X-ray tube at each of said projection angles, said projection angles including a first of said projection angles at a starting position of movement of said X-ray tube;
- a digital X-ray detector that detects X-rays attenuated by the examination object to generate respective images of the examination object at said projection angles;
- said X-ray tube, only at said first of said projection angles, irradiating the examination object with X-rays at a dose that is lower than a dose employed at others of said projection angles, to generate a preliminary image of the examination object; and
- a control and evaluation unit configured to automatically electronically evaluate said preliminary image to identify weighted doses for said X-ray tube for generating respective images in a remainder of said images, and automatically calculating the respective weighting factors at projection angles other than at said starting position as $c_k=1/\cos \alpha_k$, wherein $c_k$ is the weighting factor and $\alpha_k$ is the projection angle and to operate said X-ray tube with said weighted doses respectively at projection angles other than said first of said projection angles to generate said remainder of said images, and computationally reconstructs a digital tomosynthetic 3D X-ray image of the examination object at least from said remainder of said images.

9. A computer-readable medium encoded with a computer program, loadable into a control and evaluation unit of an apparatus for generating a digital tomosynthetic 3D X-ray image of an examination object, said apparatus comprising an X-ray tube and a digital X-ray detector, and said computer program causing apparatus to:
- move said X-ray tube through a plurality of projection angles along a circular path relative to an examination object, to irradiate the examination object with X-rays from said X-ray tube at each of said projection angles, with X-rays attenuated by the examination object being detected with said digital X-ray detector, said projection angles including a first of said projection angles at a starting position of movement of said X-ray tube;
- generate respective images of the examination object at the projection angles;
- operate said X-ray tube to irradiate the examination object, only at said first of said projection angles, with X-rays from the X-ray tube at a dose that is lower than a dose employed at others of said projection angles, to generate a preliminary image of the examination object;
- automatically electronically evaluate said preliminary image to identify weighted doses for said X-ray tube for generating respective images in a remainder of said images, and automatically calculate the respective weighting factors at projection angles other than at said starting position as $c_k=1/\cos \alpha_k$, wherein $c_k$ is the weighting factor and $\alpha_k$ is the projection angle and to operate said X-ray tube with said weighted doses respectively at projection angles other than said first of said projection angles to generate said remainder of said images; and
- computationally reconstruct a digital tomosynthetic 3D X-ray image of the examination object at least from said remainder of said images.

\* \* \* \* \*